United States Patent [19]

Chan

[11] Patent Number: 5,952,198

[45] Date of Patent: *Sep. 14, 1999

[54] PRODUCTION OF RECOMBINANT FACTOR VIII IN THE PRESENCE OF LIPOSOME-LIKE SUBSTANCES OF MIXED COMPOSITION

[75] Inventor: Sham-Yuen Chan, El Sobrante, Calif.

[73] Assignee: Bayer Corporation, Berkeley, Calif.

[*] Notice: This patent is subject to a terminal disclaimer.

[21] Appl. No.: 08/634,001

[22] Filed: Apr. 17, 1996

Related U.S. Application Data

[63] Continuation-in-part of application No. 08/434,900, May 4, 1995, Pat. No. 5,679,549.

[51] Int. Cl.[6] .......................... C07K 14/755; C12N 5/00; C12N 5/02; C12N 15/12
[52] U.S. Cl. .......................... 435/69.6; 435/383; 435/404; 935/33; 935/34; 530/383
[58] Field of Search ..................... 435/69.6, 383, 435/404, 325; 530/383; 935/33, 34

[56] References Cited

U.S. PATENT DOCUMENTS 5,198,349    3/1993    Kaufman ........................... 435/69.6

*Primary Examiner*—Dian C. Jacobson
*Attorney, Agent, or Firm*—Michael J. Beck; James A. Giblin

[57] ABSTRACT

Recombinant Factor VIII expression in a mammalian cell culture can be increased by including a novel liposome-like substance in the culture medium. The liposome-like substance comprises at least two (preferably at least three) different lipids in defined molar ratios. In a preferred embodiment, the addition of a liposome-like substance comprised of dioleoyl phosphatidylcholine, phosphatidylethanolamine, and phosphatidylserine in a molar ratio of 4:1:1 to the culture medium of GS-MDR cells resulted in an increase in FVIII production by a factor greater than five.

7 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 14
      (B) TYPE: amino acid
      (C) STRANDEDNESS: single strand
      (D) TOPOLOGY: linear (ii) MOLECULE TYPE:
      (A) DESCRIPTION: peptide (xi) SEQUENCE DESCRIPTION: SEQ ID NO:1:

Ser Phe Ser Gln Asn Pro Pro Val Leu Lys Arg His Gln Arg
1          5                   10

PRODUCTION OF RECOMBINANT FACTOR VIII IN THE PRESENCE OF LIPOSOME-LIKE SUBSTANCES OF MIXED COMPOSITION

This is a Continuation-in-Part of patent application Ser. No. 08/434,900, filed May 4, 1995 now U.S. Pat. No. 5,679,549.

BACKGROUND OF THE INVENTION

1. Field

This disclosure is concerned generally with the production of recombinant Factor VIII in a mammalian cell expression system. Specifically, the disclosure relates to the addition of a liposome-like substance containing lipids in defined ratios to the mammalian cell culture medium to increase yields of recombinant Factor VIII.

2. Background

Factor VII is a plasma protein required for normal hemostasis, or clotting of the blood. Functional Factor VIII is lacking in individuals with hemophilia A because of a mutation in the gene encoding this protein, which is located in the X-chromosome. To control bleeding episodes, hemophiliacs must be treated with Factor VIII, which historically has been isolated from human blood plasma.

The human Factor VIII gene encompasses 186,000 base pairs and constitutes 0.1% of the entire X-chromosome, making it among the largest genes known (1). The transcription product of this gene, which is derived from 26 exons, is a messenger RNA molecule of ~9000 bases in length, coding for a large protein of 2351 amino acids. Structural studies of Factor VIII indicate that it is a glycoprotein, containing a significant number of carbohydrate residues. The cDNA coding for Factor VIII has been cloned (2,3) and stably expressed in baby hamster kidney cells (BHK-21) (3) and Chinese hamster ovary cells (4). The availability of these high producing cell clones has made large-scale production of recombinant Factor VIII (rFVIII) feasible. Two significant challenges in the commercial production of rFVIII are (i) the development of a serumfree medium that will support high density cultures and stabilize rFVIII, and (ii) an efficient purification scheme that will yield high purity rFVIII.

Previously it has been demonstrated that the addition of bovine lipoprotein or human low density lipoprotein to serumfree cultures significantly improve the productivity of recombinant BHK-21 and human embryonic kidney (293S) cells expressing rFVIII (5). The co-expression of vonWillebrand factor and the addition of phospholipids to serumfree medium have been shown to be effective in enhancing the stability of rFVIII produced by rFVIII expressing CHO cells (6).

I have found that certain liposome-like substances comprising at least two (preferably at least three) lipids can be used as culture supplements in the serumfree production of rFVIII. Contrary to the prior art (6), I have observed that certain liposome-like substances comprised of lipids such as phosphatidylcholine (PC), phosphatidylethanolamine (PE), or phosphatidylserine (PS) alone have no effect on rFVIII expression in BHK-21 and 293S cells. However, liposome-like substances comprising combinations of different lipids, such as cholesterol, fatty acids such as linoleic acid and palmitic acid, PC, PE, and PS, at certain ratios were found to have a significant enhancing effect on rFVIII expression in BHK-21 and 293S cells. A serumfree production medium for long term production of rFVIII was developed from these new findings.

SUMMARY OF THE INVENTION

I have found a method and medium for substantially increasing the productivity of a mammalian cell expression system producing recombinant Factor VIII by a factor greater than about four. The essential step of the method consists of the addition of a liposome-like substance to the cell growth medium of the expression system. As used herein, "liposome-like substance" means vesicles or other tertiary-structures comprising one or more bilayers comprised of at least two different lipids in fixed molar ratios. Molar ratios should be understood to be approximate.

This invention is illustrated in the following examples, which set forth typical procedures and cell culture media for production (preferably continuous production) of rFVIII using the liposome-like substances to deliver lipid supplements to recombinant cells expressing high levels of rFVIII.

SPECIFIC EMBODIMENTS

Preparation of liposome-like substances

All synthetic phospholipids were obtained from Avanti Polar Lipids, Inc. (Alabaster, Alabama). Phospholipids were delivered as 0.1 $\mu$ liposome-like substances. Lyophilized phospholipids were reconstituted in 50 mM Tris-150 mM NaCl (pH 7.4) and extruded through a 0.1 $\mu$ polycarbonate membrane with the aid of a hand-held device—LiposoFast (Avestin, Inc., Ottawa, Canada). The sized liposome-like substances were then filtered with a 0.2 $\mu$ filter and added aseptically to culture medium. Phosphatidylethanolamine (PE), phosphatidylcholine (PC), and phosphatidylserine (PS) were examined either as single components or mixtures. Other lipids such as cholesterol and free fatty acids were also incorporated into the liposome-like substances.

EXAMPLE I

Effect of various lipid mixtures on the expression of rFVIII in 293S cells

GS-10 (recombinant 293S cells expressing high levels of Factor VIII) cells were maintained as serumfree cultures in shake flasks using a serumfree medium (Dulbecco's minimum essential medium and F12 at a ratio of 1:1, obtained from Life Technologies, Bethesda, Md.) supplemented with insulin (10$\mu$g/ml) and transferrin (25 $\mu$g/ml). Long term evaluation was done in shake flasks with an initial seeding density of 3×10$^6$ cells/ml. Complete medium exchanges were done at 24-hour intervals where cells were spun, washed and reseeded at 3×10$^6$ cells/ml. A typical shaker culture contains 25–50 ml of cells. Factor VIII activity was determined by Coatest VIII (Kabi Pharmacia, Franklin, Ohio), a chromogenic assay, according to manufacturer's instructions.

The initial screening of phospholipids was done using 24-hour plate cultures. After determining the optimal ratio of various phospholipids, the study was then confirmed in shake flasks over a period of 10–14 days. As shown in Table 1, while PC and PE alone had no effect on Factor VIII expression, PS alone was found to be inhibitory. By combining PC, PS, and PE at various ratios, significant increases in Factor VIII expression were observed. The highest productivity was observed in cells supplemented with PC:PE:PS (4:1:1), PC:PS:cholesterol (8:1:1), and PC:PS:palmitic acid:linoleic acid (7:3:0.5:0.5). The optimal concentration of phospholipids was found to be 30 $\mu$g/ml. The optimal length of the acyl side chain of various phospholipids was determined to be C18. All optimization studies were subsequently done with dioleoyl phospholipids.

EXAMPLE II

Expression of factor VIII in continuous culture

I measured the effect of various liposome-like substances on the production of factor VIII in long term shake flask cultures with PC:PE:PS (4:1:1), PC:PS: palmitic acid:linoleic acid (7:3:0.5:0.5), and PC:PS:cholesterol (8:1:1). The culture conditions were done as described in Example I. The concentration of the liposome-like substances was at 30 μg/ml. Complete medium exchange was done at 24-hour intervals. Results are shown in Table 2.

EXAMPLE III

Expression of Factor Vil in continuous cultures

The effect of various liposomes on the production of truncated Factor VIII (deletion of all or part of the B domain of Factor VIII) was examined in recombinant 293S cells expressing high levels of a B-domain-deleted Factor VIII with the following sequence (SEQ ID NO. 1) joining the 90-kD and 80-kD fragments of Factor VIII:

"90kD—Ser-Phe-Ser-Gln-Asn-Pro-Pro-Val-Leu-Lys-Arg-His-Gln-Arg—80kD (SEQ ID NO:1)". (Amino acid abbreviations are as given in Ref. (7), incorporated herein by reference.) This truncated Factor VIII is essentially as described in Ref. (8), incorporated herein by reference. The culture conditions were done in 12-well plates with an initial seeding density of 2×105 cells per well in DMEM/F12 (1:1) supplemented with 5% fetal bovine serum. After confluency was reached the cells were washed with PBS and fed with the serumfree production as described in Example I. Results are shown in Table 3, where at least a threefold increase in productivity over the saline control is shown. The highest productivites were observed in cells supplemented with dioleoyl PC/PE/PS (8:1:1) and dioleoyl PC/PS/cholesterol (8:1:1).

CONCLUSION

We have demonstrated that lipid mixtures, when delivered in the form of liposome-like substances, significantly enhance the production of Factor VIII (in both full length and truncated forms) in recombinant cells. These liposome-like substances can be used as medium supplements to support production of Factor VIII, preferably continuous production of Factor VIII. As used herein, the term Factor VIII is intended to include all variants or truncated forms of Factor VIII having Factor VIII activity.

The above examples are intended to illustrate the invention and it is thought variations will occur to those skilled in the art. Accordingly, it is intended that the scope of the invention should be limited only by the claims below.

TABLE 1

Effect of phospholipid on the expression of Factor VIII in GS-MDR cells

| Phospholipids | FVIII Titer (U/ml) |
| --- | --- |
| Dioleoyl PC/PS (7:3) | 2.8 |
| Dioleoyl PC/PS (8:2) | 2.5 |
| Dioleoyl PC/PS (9:1) | 1.4 |
| Dioleoyl PC/PS/palmitic/linoleic acid (7:3:0.5:0.5) | 3.4 |
| Dioleoyl PC/PE/PS (4:1:1) | 3.5 |

TABLE 1-continued

Effect of phospholipid on the expression of Factor VIII in GS-MDR cells

| Phospholipids | FVIII Titer (U/ml) |
| --- | --- |
| Dioleoyl PC/PE/PS (8:1:1) | 1.7 |
| DioleoylPC/PE/PS (16:1:2) | 2.1 |
| Dioleoyl PC | 0.65 |
| Dioleoyl PE | 0.55 |
| Dioleoyl PS | 0.15 |
| Saline | 0.60 |

TABLE 2

Production of Factor VIII in continuous cultures of GS-10 cells

FVIII titer (U/ml)

| Days | PC/PE/PS (4:1:1) | PC/PS/pm/ln (7:3:0.5:0.5) | PC/PS/Cholesterol (8:1:1) | Medium only |
| --- | --- | --- | --- | --- |
| 1 | 2.44 | 2.51 | 2.41 | 0.35 |
| 2 | 2.78 | 2.89 | 2.72 | 0.4 |
| 3 | 2.46 | 2.77 | 2.69 | 0.44 |
| 4 | 2.82 | 2.8 | 2.7 | 0.48 |
| 5 | 2.88 | 2.95 | 2.99 | 0.42 |
| 6 | 2.9 | 3.1 | 2.95 | 0.41 |
| 7 | 3.21 | 3.18 | 3.12 | 0.54 |
| 8 | 3.18 | 3.22 | 3.06 | 0.55 |
| 9 | 3.02 | 3.16 | 3.14 | 0.58 |
| 10 | 3.34 | 3.38 | 3.27 | 0.53 |
| 11 | 2.97 | 3.15 | 3.19 | 0.49 |
| 12 | 3.12 | 2.95 | 2.98 | 0.52 |
| 13 | 3.02 | 3.12 | 2.71 | 0.54 |
| 14 | 2.89 | 3.16 | 3.22 | 0.56 |
| 15 | 3.22 | 3.38 | 3.34 | 0.51 | pm = palmitic acid
ln = linoleic acid

TABLE 3

Effect of phospholipid on the expression of a B-domain deleted Factor VIII variant in 293S cells

| Phospholipids | FVIII Titer (U/ml) |
| --- | --- |
| Dioleoyl PC/PS (7:3) | 2.80 |
| Dioleoyl PC/PS (9:1) | 0.85 |
| Dioleoyl PC/PS/Cholesterol (8:1:1) | 4.0 |
| Dioleoyl PC | 1.0 |
| Dioleoyl PC/PE/PS (8:1:1) | 3.04 |
| Saline | 0.9 |

REFERENCES

1. Gitschier et al. 1984 Nature 312:326–329

2. Wood et al. 1984 Nature 312:330–337

3. Toole et al. 1984 Nature 312:342–347

4. Kaufman et al. 1989 Mol. Cell Biol. 9:1233–1242

5. Chan et al. 1991 In Vitro 27:121

6. Kaufman et al. 10/1993 U.S. Pat. No. 5,250,421

7. Scholz et al. 5/1993 U.S. Pat. No. 5,210,075

8. Almstedt et al. 6/1991 WO 91/09122

What is claimed is:

1. A method for increasing the production level of recombinant factor VIII in a mammalian cell culture expression system by at least fourfold, comprising the step of adding to the culture system a liposome-like substance comprising at least 2 different lipids in a molar ratio under conditions sufficient to assure the fourfold increase in productivity, wherein the lipids in the molar ratio are selected from the group consisting of phosphatidylcholine, phosphatidylethanolamine. and phosphatidylserine in a molar ratio of about 4:1:1, phosphatidylcholine, phosphatidvlserine and cholesterol in a molar ratio of about 8:1:1, and phosphatidylcholine, phosphatidvlserine, palmitic acid, and linoleic acid in a molar ratio of about 7:3:0.5:0.5.

2. The method of claim 1 wherein the recombinant factor VIII is truncated.

3. The method of claim 2 wherein the truncated factor VIII has a 90 kD fragment and an 80 kD fragment which are linked by a polypeptide having a sequence Ser-Phe-Ser-Gln-Asn-Pro-Pro-Val-Leu-Lys-Arg-His-Gln-Arg (SEQ ID NO: 1).

4. A culture medium containing a liposome-like substance, wherein said liposome-like substance comprises at least 2 different lipids in a molar ratio sufficient to assure at least a fourfold increase in factor VIII expression in a mammalian cell culture system, wherein the lipids in the molar ratio are selected from the group consisting of phosphatidylcholine, phosphatidylethanolamine, and phosphatidylserine in a molar ratio of about 4:1:1, phosphatidylcholine, phosphatidylserine and cholesterol in a molar ratio of about 8:1:1, and phosphatidylcholine, phosphatidylserine, palmitic acid, and linoleic acid in a molar ratio of about 7:3:0.5:0.5.

5. The medium of claim 4 wherein the recombinant factor VIII is truncated.

6. The medium of claim 5 wherein the truncated factor VIII has a 90 kD fragment and an 80 kD fragment which are linked by a polypeptide having a sequence Ser-Phe-Ser-Gln-Asn-Pro-Pro-Val-Leu-Lys-Arg-His-Gln-Arg (SEQ ID NO: 1).

7. A method for increasing the production level of a truncated recombinant factor VIII in a mammalian cell culture expression system by at least threefold, comprising the step of adding to the culture system a liposome-like substance under conditions sufficient to assure the threefold increase in productivity, wherein the liposome like substance is comprised of phosphstidylcholine, phosphatidylethanolamine, and phosphatidylserine in a molar ratio of about 8:1:1.

* * * * *